(12) United States Patent
O'Brien

(10) Patent No.: US 7,388,049 B2
(45) Date of Patent: *Jun. 17, 2008

(54) POLYETHER SILOXANE COPOLYMER NETWORK COMPOSITIONS

(75) Inventor: Michael Joseph O'Brien, Clifton Park, NY (US)

(73) Assignee: Momentive Performance Materials Inc., Wilton, CT (US)

( * ) Notice: Subject to any disclaimer, the term of this patent is extended or adjusted under 35 U.S.C. 154(b) by 112 days.

This patent is subject to a terminal disclaimer.

(21) Appl. No.: 11/262,355

(22) Filed: Oct. 28, 2005

(65) Prior Publication Data

US 2006/0052520 A1 Mar. 9, 2006

Related U.S. Application Data

(63) Continuation-in-part of application No. 10/922,487, filed on Aug. 20, 2004, now abandoned, which is a continuation of application No. 10/439,857, filed on May 16, 2003, now Pat. No. 7,241,835, which is a continuation-in-part of application No. 10/393,858, filed on Mar. 21, 2003, now Pat. No. 6,759,479, which is a continuation-in-part of application No. 09/858,795, filed on May 16, 2001, now Pat. No. 6,538,061.

(51) Int. Cl.
*C08L 83/12* (2006.01)

(52) U.S. Cl. .................... 524/837; 528/25; 528/27; 528/31

(58) Field of Classification Search .................. None
See application file for complete search history.

(56) References Cited

U.S. PATENT DOCUMENTS

| 3,996,195 | A * | 12/1976 | Sato et al. | 528/31 |
| 5,866,261 | A * | 2/1999 | Kerr et al. | 428/447 |
| 6,531,540 | B1 * | 3/2003 | O'Brien | 524/806 |
| 6,538,061 | B2 * | 3/2003 | Chaiyawat et al. | 524/806 |
| 6,759,479 | B2 * | 7/2004 | O'Brien | 524/837 |
| 2005/0197477 | A1 * | 9/2005 | O'Brien | 528/12 |
| 2006/0052521 | A1 * | 3/2006 | O'Brien | 524/588 |
| 2006/0079633 | A1 * | 4/2006 | O'Brien et al. | 524/588 |

* cited by examiner

*Primary Examiner*—Marc S Zimmer
(74) *Attorney, Agent, or Firm*—Kenneth S. Wheelock

(57) ABSTRACT

A composition comprising the reaction products of $$M_a M^H_b M^E_c D_d D^H_e D^E_f T_g T^H_h T^E_i Q_j$$

where
$M = R^1 R^2 R^3 SiO_{1/2}$;
$M^H = R^4 R^5 H\, SiO_{1/2}$;
$M^E = R^6 R^7 R^E SiO_{1/2}$;
$D = R^8 R^9 SiO_{2/2}$;
$D^H = R^{10} H SiO_{2/2}$;
$D^E = R^{11} R^E SiO_{2/2}$;
$T = R^{12} SiO_{3/2}$;
$T^H = H SiO_{3/2}$;
$T^E = R^E SiO_{3/2}$; and
$Q = SiO_{4/2}$;

where $R^1, R^2, R^3, R^8, R^9$ and $R^{12}$ are independently monovalent hydrocarbon radicals having from one to sixty carbon atoms; $R^4, R^5$ and $R^{10}$ are independently monovalent hydrocarbon radicals having from one to sixty carbon atoms or hydrogen; $R^6, R^7, R^{11}$ are independently monovalent hydrocarbon radicals having from one to sixty carbon atoms or $R^E$; each $R^E$ is independently a monovalent hydrocarbon radical containing one or more oxirane moieties having from one to sixty carbon atoms; the stoichiometric subscripts a, b, c, d, e, f, g, h, i, and j are either zero or positive subject to the following limitations: a+b+c>1;b+e+h>1;c+f+i>1;b+e+h>c+f+i. In a preferred embodiment the reaction product of the present invention is a polyether siloxane copolymer network. In another preferred embodiment the reaction product of the present invention is a polyether siloxane copolymer network swollen with a volatile low molecular weight silicon containing compound. These compositions are useful for a variety of personal care compositions.

50 Claims, No Drawings

POLYETHER SILOXANE COPOLYMER NETWORK COMPOSITIONS

CROSS-REFERENCE TO RELATED APPLICATIONS

The present application is a Continuation-in-Part Application of U.S. Ser. No. 10/922,487 filed Aug. 20, 2004 now abandoned which is a Continuation Application of U.S. Ser. No. 10/439,857 filed May 16, 2003 now U.S Pat. No. 7,241,835 which is a Continuation-In-Part Application of U.S. Ser. No. 10/393,858 filed Mar. 21, 2003, now U.S. Pat. No. 6,759,479 which is a Continuation-In-Part Application of U.S. Ser. No. 09/858,795 filed May 16, 2001 now U.S. Pat. No. 6,538,061.

FIELD OF THE INVENTION

The present invention relates to silicone compositions, more particularly to compositions comprising a silicone polymer network comprising cross-links derived from epoxide or oxirane moieites.

BACKGROUND OF THE INVENTION

The personal care industry thrives on being able to deliver multiple performance products based on mixtures of several components, with each having performance characteristics important to or desirable in the final formulation. One desirable characteristic is the ability to provide a silky initial feel derived from low molecular weight silicones, such as for example, octamethylcyclotetrasilioxane or decamethylcyclopentasiloxane, in the formulation while maintaining a high, but shear-thinnable viscosity. While these low molecular weight silicones provide the desired feel characteristics, they are also low viscosity, highly flowable liquids. Thus they are not easily held in a formulation, preferring rather to separate and flow out of a given container or flow uncontrollably across the skin when used in a specific application. Further, it is desirable to achieve an initial silky feel while providing a smooth, low-residue feel upon dry-down. Polymeric silicone gels prepared in volatile silicone have been found to deliver desirable initial feel of volatile, low viscosity silicones to formulations while at the same time provide high viscosity and a smooth silky feel on dry-down, see for example, U.S. Pat. Nos. 5,760,116, 5,493,041 and 4,987,169.

Such polymeric silicone gels have typically been made by the hydrosilylation reaction, which requires the use of both SiH functional groups and terminal olefinic groups to form crosslinked siloxane polymers. Thus only siloxane structures that can incorporate silylhydride groups and optionally, vinyl functional siloxane groups, can be utilized in making these materials. Further this method of generating crosslinked siloxane polymers limits the range of desirable organofunctional groups that may be incorporated into the polymeric structure to create additional performance advantages in complex formulations. Thus attempts to include organofunctional groups into the crosslinked siloxane polymer include unsaturated organic groups compatible with the hydrosilylaton reaction.

SUMMARY OF THE INVENTION

A composition comprising the reaction products of $$M_a M^H{}_b M^E{}_c D_d D^H{}_e D^E{}_f T_g T^H{}_h T^E{}_i Q_j.$$

where
$M = R^1 R^2 R^3 SiO_{1/2}$;
$M^H = R^4 R^5 H\ SiO_{1/2}$;
$M^E = R^6 R^7 R^E SiO_{1/2}$;
$D = R^8 R^9 SiO_{2/2}$;
$D^H = R^{10} H SiO_{2/2}$;
$D^E = R^{11} R^E SiO_{2/2}$;
$T = R^{12} SiO_{3/2}$;
$T^H = H SiO_{3/2}$;
$T^E = R^E SiO_{3/2}$; and
$Q = SiO_{4/2}$;

where $R^1$, $R^2$, $R^3$, $R^8$, $R^9$ and $R^{12}$ are independently monovalent hydrocarbon radicals having from one to sixty carbon atoms; $R^4$, $R^5$ and $R^{10}$ are independently monovalent hydrocarbon radicals having from one to sixty carbon atoms or hydrogen; $R^6$, $R^7$, $R^{11}$ are independently monovalent hydrocarbon radicals having from one to sixty carbon atoms or $R^E$; each $R^E$ is independently a monovalent hydrocarbon radical containing one or more oxirane moieties having from one to sixty carbon atoms; the stoichiometric subscripts a, b, c, d, e, f, g, h, i, and j are either zero or positive subject to the following limitations: a+b+c>1; b+e+h>1; c+f+i>1; b+e+h>c+f+i. In a preferred embodiment the reaction product of the present invention is a polyether siloxane copolymer network. In another preferred embodiment the reaction product of the present invention is a polyether siloxane copolymer network swollen with a volatile low molecular weight silicon containing compound. These compositions are useful for a variety of personal care compositions.

DETAILED DESCRIPTION OF THE INVENTION

The compositions of the present invention comprise the reaction products of an epoxy functional hydrido siloxane molecule having the following formula:

$$M_a M^H{}_b M^E{}_c D_d D^H{}_e D^E{}_f T_g T^H{}_h T^E{}_i Q_j$$

where
$M = R^1 R^2 R^3 SiO_{1/2}$;
$M^H = R^4 R^5 H\ SiO_{1/2}$;
$M^E = R^6 R^7 R^E SiO_{1/2}$;
$D = R^8 R^9 SiO_{2/2}$;
$D^H = R^{10} H SiO_{2/2}$;
$D^E = R^{11} R^E SiO_{2/2}$;
$T = R^{12} SiO_{3/2}$;
$T^H = H SiO_{3/2}$;
$T^E = R^E SiO_{3/2}$; and
$Q = SiO_{4/2}$;

where $R^1$, $R^2$, $R^3$, $R^8$, $R^9$ and $R^{12}$ are independently monovalent hydrocarbon radicals having from one to sixty carbon atoms; $R^4$, $R^5$ and $R^{10}$ are independently monovalent hydrocarbon radicals having from one to sixty carbon atoms or hydrogen; $R^6$, $R^7$, $R^{11}$ are independently monovalent hydrocarbon radicals having from one to sixty carbon atoms or $R^E$; each $R^E$ is independently a monovalent hydrocarbon radical containing one or more oxirane moieties having from one to sixty carbon atoms; the stoichiometric subscripts a, b, c, d, e, f, g, h, i, and j are either zero or positive subject to the following limitations: a+b+c>1; b+e+h>1; c+f+i>1; b+e+h>c+f+i.

One method of producing the composition of the present invention is to react a molecule having the following formula:

$$M_a M^H{}_b D_d D^H{}_e T_g T^H{}_h Q_j$$

wherein the definitions and relationships are as later defined (and also consistent with those defined above) under hydrosilylation conditions with an olefinically unsaturated molecule containing one or more oxirane moieties under conditions of stoichiometry where the molar quantity of oxirane is less than the molar quantity of silyl hydride. As used herein the phrase "an olefinically unsaturated molecule containing one or more oxirane moieties" means a molecule possessing one or more interior, pendant or terminal carbon carbon double bonds simultaneously with one or more interior, pendant or terminal three membered oxygen containing heterocyclic rings (chemically the phrase "three membered oxygen containing heterocyclic ring" is used herein interchangeably with the oxirane or epoxide structures). The simplest chemical structure exemplified by such a definition is:

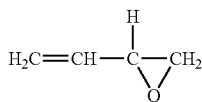

but also includes alicyclic structures exemplified by:

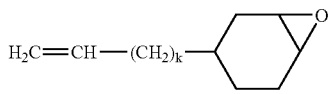

where the subscript k may be zero or a positive integer, more preferably a positive integer ranging generally from 0 to about 10. It should be noted that both exemplified structures are terminal in both the olefinic moiety and the oxirane (epoxide) moiety. A more general chemical structure is:

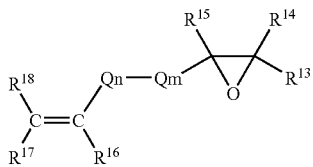

where $R^{13}$, $R^{14}$, $R^{15}$, $R^{16}$, $R^{17}$ and $R^{18}$ are each independently selected from the group of hydrogen and monovalent hydrocarbon radicals having from one to sixty carbon atoms, $Q_m$ is a di- or trivalent hydrocarbon radical having from one to sixty carbon atoms, $Q_n$ is a divalent hydrocarbon radical having from one to sixty carbon atoms with the subscripts m and n independently zero or one subject to the limitation that when Qm is trivalent one of $R^{13}$ or $R^{14}$ is absent and where $R^{16}$ and $R^{18}$ may be either cis- or trans- to each other.

Thus one possible synthetic pathway to prepare the reaction products of the present invention is as follows:

$M_a M^H_{b'} D_d D^H_{e'} T_g T^H_{h'} Q_j$ + α

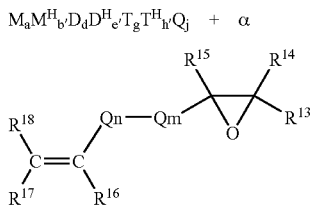

reacting under hydrosilylation conditions to yield $M_a M^H_b M^E_c D_d D^H_e D^E_f T_g T^H_h T^E_i Q_j$ when the stoichiometric coefficient, α, is less than the sum of b'+e'+h'. It should be noted that the stoichiometric coefficients b, e, and h define the quantity of hydride bearing species $M^H$, $D^H$ and $T^H$ in both reactant and product and are related one to other in that fashion but because some of the hydride bearing functions have reacted with an olefinically unsaturated molecule containing one or more oxirane moieties the following relationships must necessarily obtain: b'+e'+h'>b+e+h and b+c+e+f+h+i=b'+e'+h'. It is to be noted that acetylene analogs of the olefinically unsaturated oxirane containing molecules will produce similar species that will react to form similar products. Thus as used herein the phrase an olefinically unsaturated molecule containing one or more oxirane moieties is intended to also include an acetylenically unsaturated molecule containing one or more oxirane moieties. The phrase "an acetylenically unsaturated molecule containing one or more oxirane moieties" means a molecule possessing one or more interior, pendant or terminal carbon carbon triple bonds simultaneously with one or more interior, pendant or terminal three membered oxygen containing heterocyclic rings (chemically the phrase "three membered oxygen containing heterocyclic ring" is used herein interchangeably with the oxirane or epoxide structures). When the epoxide compound is an olefinic epoxide, a specific example being:

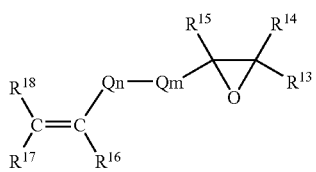

then $R^E$ as a substituent, becomes

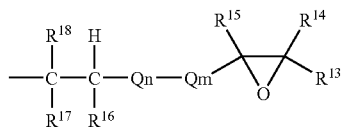

with all the definitions consistent with those as previously defined. When the epoxide is an acetylenic epoxide, a specific example being:
or

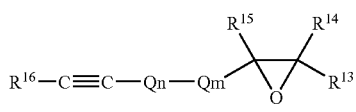

then $R^E$ as a substituent, becomes either:

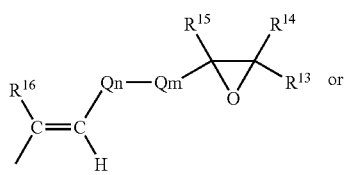

-continued

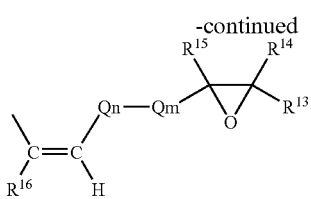

with all the definitions consistent with those as previously defined.

The silyl hydride bearing precursor molecule, $M_aM^H_bD_dD^H_eT_gT^H_hQ_j$, can be prepared by a variety of techniques known in the art. Epoxy substituted siloxanes are prepared in the normal manner through the use of a hydrosilylation reaction to attach a vinyl or allyl substituted epoxide onto an SiH bearing siloxane. SiH containing siloxanes are well known in the art and can be linear, branched, or cyclic in structure. Examples of useful vinyl or allyl substituted epoxides include 4-vinyl cyclohexene oxide, allyl glycidyl ether, limonene oxide, 1,2-epoxy-5-hexene, 1,2-epoxy-7-octene, norbornadiene monoepoxide and 1,2-epoxy-9-decene. Precious metal catalysts suitable for making epoxy siloxanes are also well known in the art and comprise complexes of rhodium, ruthenium, palladium, osmium, iridium and/or platinum.

Many types of platinum catalysts for this SiH olefin addition reaction (hydrosilation or hydrosilylation) are known and such platinum catalysts may be used for the reaction in the present instance. When optical clarity is required the preferred platinum catalysts are those platinum compound catalysts that are soluble in the reaction mixture. The platinum compound can be selected from those having the formula (PtCl$_2$Olefin) and H(PtCl$_3$Olefin) as described in U.S. Pat. No. 3,159,601, hereby incorporated by reference. A further platinum containing material usable in the compositions of the present invention is the cyclopropane complex of platinum chloride described in U.S. Pat. No. 3,159,662 hereby incorporated by reference. Further the platinum containing material can be a complex formed from chloroplatinic acid with up to 2 moles per gram of platinum of a member selected from the class consisting of alcohols, ethers, aldehydes and mixtures of the above as described in U.S. Pat. No. 3,220,972 hereby incorporated by reference. The catalysts preferred for use are described in U.S. Pat. Nos. 3,715,334; 3,775,452; and 3,814,730 to Karstedt. Additional background concerning the art may be found at J. L. Spier, "Homogeneous Catalysis of Hydrosilation by Transition Metals, in *Advances in Organometallic Chemistry*, volume 17, pages 407 through 447, F. G. A. Stone and R. West editors, published by the Academic Press (New York, 1979). Persons skilled in the art can easily determine an effective amount of platinum catalyst. Generally, an effective amount ranges from about 0.1 to 50 parts per million of the total organopolysiloxane composition.

The reaction product of $M_aM^H_bM^E_cD_dD^H_eD^E_fT_gT^H_hT^E_iQ_j$ produces a polymer network, believed to be a polyether siloxane copolymer network (or alternatively a siloxane polyether copolymer network). As used herein, the terminology "network" means a three dimensionally extending structure comprising interconnected polyether siloxane copolymer chains. Preferably, fluid is contained within interstices of the network. The term "interstices" is used herein in reference to a network to denote spaces within the network, that is, spaces between the polyether siloxane copolymer chains of the network. As used herein in the context of the polyether siloxane copolymer network, the term polyether is intended to include the reaction product of two or more epoxide moieties to form one or more ether linkages that form a cross link between siloxane chains or moieties.

In one preferred embodiment, the polyether siloxane copolymer network is a crosslinked network that is insoluble in the fluid component of the silicone composition of the present invention, but that is capable of being swollen by the fluid. The amount of crosslinking present in the crosslinked network may be characterized with respect to the degree of swelling exhibited by the network in the fluid. In another preferred embodiment, the crosslinked structure of the network is effective to allow the network to be swollen by a low molecular weight fluid or silicone fluid, such as, for example, decamethylcyclopentasiloxane, from its original volume to a swollen volume that is a factor of from 1.01 to 5000, more preferably from 2 to 1000, and even more preferably from 5 to 500, times its original volume. The original volume of the network can be determined, for example, by extracting or evaporating all of the fluid component from the silicone composition of the present invention to leave the original volume, that is, the volume of the polyether siloxane copolymer network in the absence of the fluid.

As used herein the terminology "hydrocarbon radical" includes acyclic hydrocarbon radicals, alicyclic hydrocarbon radicals and aromatic hydrocarbon radicals.

As used herein in reference to a hydrocarbon radical, the term "monovalent" means that the radical is capable of forming one covalent bond per radical, the term "divalent" means that the radical is capable of forming two covalent bonds per radical and the term "trivalent" means that the radical is capable of forming three covalent bonds per radical. Generally, a monovalent radical can be represented as having been derived from a saturated hydrocarbon compound by conceptual removal of one hydrogen atom from the compound, a divalent radical can be represented as having been derived from a saturated hydrocarbon compound by conceptual removal of two hydrogen atoms from the compound and a trivalent radical can be represented as having been derived from a saturated hydrocarbon compound by conceptual removal of three hydrogen atoms from the compound. For example, an ethyl radical, that is, a —CH$_2$CH$_3$ radical, is a monovalent radical; a dimethylene radical, that is, a —(CH$_2$)$_2$— radical, is a divalent radical and an ethanetriyl radical, that is,

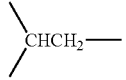

radical, is a trivalent radical, each of which can be represented as having been derived by conceptual removal of one or more hydrogen atoms from the saturated hydrocarbon ethane.

As used herein, the terminology "acyclic hydrocarbon radical" means a straight chain or branched hydrocarbon radical, preferably containing from 1 to 60 carbon atoms per radical, which may be saturated or unsaturated and which may be optionally substituted or interrupted with one or more atoms or functional groups, such as, for example, carboxyl, cyano, hydroxy, halo and oxy. As long as these functional groups do not interfere with the cationic cure mechanism of the epoxide or oxirane moiety, suitable monovalent acyclic hydrocarbon radicals may include, for example, alkyl, alkenyl, alkynyl, hydroxyalkyl, cyanoalkyl, carboxyalkyl, alkyloxy, oxaalkyl, alkylcarbonyloxaalkylene, carboxamide and haloalkyl, such as, for example, methyl, ethyl, sec-butyl, tert-butyl, octyl, decyl, dodecyl, cetyl, stearyl, ethenyl, propenyl, butynyl, hydroxypropyl, cyanoethyl, butoxy, 2,5,8-trioxadecanyl, carboxymethyl, chloromethyl and 3,3,3-fluoropropyl. Suitable divalent acyclic hydrocarbon radicals include, for example, linear or branched alkylene radicals, such as, for example, methylene, dimethylene, trimethylene, decamethylene, ethylethylene, 2-methyltrimethylene, 2,2-dimethyltrimethylene and linear or branched oxalkylene radicals such as, for example, methyleneoxypropylene. Suitable trivalent acyclic hydrocarbon radicals include, for example, alkanetriyl radicals, such as, for example, 1,1,2-ethanetriyl, 1,2,4-butanetriyl, 1,2,8-octanetriyl, 1,2,4-cyclohexanetriyl and oxaalkanetriyl radicals such as, for example, 1,2,6-triyl-4-oxahexane.

As used herein the term "alkyl" means a saturated straight or branched monovalent hydrocarbon radical. In a preferred embodiment, monovalent alkyl groups are selected from linear or branched alkyl groups containing from 1 to 60 carbons per group, such as, for example, methyl, ethyl, propyl, isopropyl, n-butyl, iso-butyl, sec-butyl, tert-butyl, pentyl, hexyl, heptyl, decyl, dodecyl.

As used herein the term "alkenyl" means a straight or branched monovalent terminally unsaturated hydrocarbon radical, preferably containing from 2 to 10 carbon atoms per radical, such as, for example, ethenyl, 2-propenyl, 3-butenyl, 5-hexenyl, 7-octenyl and ethenylphenyl.

As used herein, the terminology "alicyclic hydrocarbon radical" means a radical containing one or more saturated hydrocarbon rings, preferably containing from 4 to 12 carbon atoms per ring, per radical which may optionally be substituted on one or more of the rings with one or more alkyl radicals, each preferably containing from 2 to 6 carbon atoms per alkyl radical, halo radicals or other functional groups and which, in the case of a monovalent alicyclic hydrocarbon radical containing two or more rings, may be fused rings. Suitable monovalent alicyclic hydrocarbon radicals include, for example, cyclohexyl and cyclooctyl. Suitable divalent hydrocarbon radicals include, saturated or unsaturated divalent monocyclic hydrocarbon radicals, such as, for example, 1,4-cyclohexylene. Suitable trivalent alicyclic hydrocarbon radicals include, for example, cycloalkanetriyl radicals such as, for example, 1-dimethylene-2,4-cyclohexylene, 1-methylethylene-3-methyl-3,4-cyclohexylene.

As used herein, the terminology "aromatic hydrocarbon radical" means a hydrocarbon radical containing one or more aromatic rings per radical, which may, optionally, be substituted on the aromatic rings with one or more alkyl radicals, each preferably containing from 2 to 6 carbon atoms per alkyl radical, halo radicals or other functional groups and which, in the case of a monovalent aromatic hydrocarbon radical containing two or more rings, may be fused rings. Suitable monovalent aromatic hydrocarbon radicals include, for example, phenyl, tolyl, 2,4,6-trimethylphenyl, 1,2-isopropylmethylphenyl, 1-pentalenyl, naphthyl, anthryl, eugenol and allylphenol as well as aralkyl radicals such as, for example, 2-phenylethyl. Suitable divalent aromatic hydrocarbon radicals include, for example, divalent monocyclic arenes such as, for example, 1,2-phenylene, 1,4-phenylene, 4-methyl-1,2-phenylene, phenylmethylene. Suitable trivalent aromatic hydrocarbon radicals include, for example, trivalent monocyclic arenes such as, for example, 1-trimethylene-3,5-phenylene.

In a preferred embodiment, the epoxy functional organosiloxane compound is reacted by polymerizing the epoxy functional organosiloxane compound under cationic polymerization conditions and, preferably, in the presence of a fluid, preferably a volatile siloxane fluid. In one embodiment, the epoxy functional organosiloxane compound is polymerized in the presence of a fluid to directly form the silicone composition of the present invention. In another embodiment, the epoxy functional organosiloxane compound is polymerized in the presence of a first fluid or fluid mixture to form a polyether siloxane copolymer network, and then the network so formed is subsequently swollen with a second fluid or fluid mixture to form the silicone composition of the present invention. The second fluid or fluid mixture may be the same as or different from the first fluid mixture. The first solvent may, optionally, be removed from the polymerized network by, for example, evaporation, prior to addition of the second fluid. As a further alternative, the epoxy functional organosiloxane compound is polymerized in the absence of a fluid to form a polyether siloxane copolymer network and the network is subsequently swollen with a fluid or mixture of fluids to form the silicone composition of the present invention. In another embodiment, the polymerization of the epoxy functional organosiloxane is conducted with a sufficient amount of excess hydridosiloxane functionality such that there is residual hydride remaining after polymerization that may be subsequently reacted under conditions suitable for hydrosilylation with one or more alkenyl functional compounds. This is especially advantageous in cases where the alkenyl functional compounds can act as inhibitors of cationic cure. Such alkenyl compounds are those that contain a functionality that can act as an inhibitor of the cationic cure mechanism, e.g. a base. In another embodiment, a small amount of a concentrated hydridosiloxane or hydridosilane compound is added in order to increase the rate of polymerization.

Cationic polymerization conditions can be generated by addition of an acid catalyst capable of polymerizing an epoxy group such as, for example, by addition of onium salt generated acids and certain metal salts, such as, for example, aluminum trichloride and ferric chloride, which act as Lewis acids or by addition of lanthanide triflates, see PCT Int. Appl. WO 0008,087. Acid catalyzed polymerization of epoxides is a well known method of forming organic polymers and has been applied to epoxy-functional siloxane compounds in order to form siloxane polyalkyleneoxide block copolymers for use in a variety of applications as, for example, release coatings on paper, see, for example, U.S. Pat. No. 4,279,717, and in conjunction with organic materials to form coatings and modified plastic compositions, see for example, U.S. Pat. Nos. 5,354,796 and 5,663,752. One precautionary note must be observed, that is if the cationic polymerization is conducted in the presence of cyclic siloxanes, e.g. $D_3$, $D_4$ or $D_5$ and the like, the strength of the acid catalysis employed must be such that cationic polymerization of the epoxide moiety occurs but polymerization of the cyclic siloxane does not occur to any appreciable extent.

In a preferred embodiment, the epoxy functional organosiloxane compound is polymerized under cationic cure conditions generated through the interaction with platinum and an SiH-containing compound. This epoxide polymerization reaction route is described in U.S. Pat. No. 5,128,431 and by J. V. Crivello and N. Fan, J. Polymer Sci., Part A: Polymer Chemistry, pp. 1853-1863 (1997). In this embodiment, the reaction kinetics appear to be dependent upon the presence of trace quantities of molecular oxygen.

The polyether siloxane copolymer network compositions of the present invention produce a cross linked structure that possesses a certain amount of steric hindrance by reason of the cross links. This steric hindrance tends to prevent the reaction from going to completion even at long reaction times and thus a certain amount of residual functionality may remain. This residual functionality provides the ability to incorporate other functionality into the polyether siloxane copolymer network by reaction with functionalized molecules that are not as sterically constrained as the polyether siloxane copolymer network or it must be chemically inactivated. One reason the residual functionality might desirably be chemically inactivated is that in the processing of these materials as a polyether siloxane copolymer network swollen with a low molecular weight siloxane compound (or alternatively, low molecular weight silicone fluid), usually $D_3$, $D_4$, $D_5$, $D_6$ or $M'D'_qT'_sM'$ as later defined, is that processing under conditions of high shear tends to disrupt the network reducing the level of steric hindrance and thus could enable further cross linking reactions to occur because of the chemically exposed residual functionality. Post-cure cross linking is known to occur in addition polymerized silicones where the addition polymerization occurs via hydrosilylation. These materials are prepared by first hydrosilylation of a silyl hydride with an olefinic or acetylenic oxirane or epoxide compound. Thus a noble metal hydrosilylation catalyst will be present in the reaction mixture or within the interstices of the polyether siloxane copolymer network. This catalyst may be used to further polymerize the oxirane or epoxide moiety (moieties) incorporated in the reaction product producing the polyether siloxane copolymer network(s) of the present invention. The residual functionality remaining by design, i.e. by use of sub-stoichiometric quantities, or by reason of steric inhibition of reaction completion may be further reacted as taught herein or neutralized or inhibited. U.S. Pat. Nos. 5,977, 280 and 5,929,164, both herein incorporated by reference, teach such neutralization of hydrosilylation catalysts by treatment with strong noble metal complexing ligands, for example phosphines, amines and organic sulfur compounds such as organic sulfides and thiols. However, some of these strongly complexing ligands, while deactivating a noble metal hydrosilylation catalyst are toxic and thus their use must be avoided in some applications, e.g. personal care applications. Thus sulfur containing amino acid esters are strong noble metal complexing ligands and methionine methyl ester, methionine ethyl ester, cysteine methyl ester, cysteine ethyl ester and cysteine dimethyl ester have been preferred for such noble metal deactivation. It should be noted that naturally occurring proteins containing disulfide linkages that are easily disrupted may also be used to deactivate the noble metal catalysts employed, e.g. egg yolks and the like. Sulfur containing amino acid amides, polypeptides and the like may also function similarly to deactivate noble metal hydrosilylation catalysts.

The method of polymer synthesis provides for incorporation of a wide range of organofunctional groups into the copolymeric structure. Thus, the inclusion of other organofunctional groups, such as, for example, organic epoxides, epoxysiloxanes, terminally unsaturated organic and alkenylsiloxane compounds can be used to modify the resulting copolymers.

In an alternative embodiment, the organofunctional groups are introduced to the network during polymerization of the epoxyfunctional organosiloxane by including organofunctional compounds to the reaction mixture which are copolymerizable with the epoxy functional organosiloxane under the chosen polymerization reaction conditions.

In one embodiment, polymerization of the epoxy functional organosiloxane is conducted in the presence of one or more organic epoxide compounds which are copolymerizable with epoxy functional hydrido siloxanes under the polymerization conditions to form mixed polyalkyleneoxide units. The additional organic epoxide compounds may contain different substituents to further modify the resulting copolymer. Suitable organic epoxide compounds include, for example, ethylene oxide, propylene oxide, butylene oxide, cyclohexene oxide, glycidol and epoxide oils such as for example epoxidized soybean oil.

In another embodiment, the polymerization of the epoxy functional organosiloxane is conducted in the presence of one or more hydroxyl functional compounds which are copolymerizable with epoxy functional hydrido siloxanes under the polymerization conditions to modify the product copolymer. Suitable hydroxyl functional compounds include, for example, water, hydroxy-stopped polyethers, organic alcohols, including organic diols, carbinol functional siloxanes and hydroxy functional organopolysiloxane polymers, including polyethersiloxane copolymers.

In another embodiment, the polymerization of the epoxy functional organosiloxane is conducted in the presence one or more alkenyl functional compounds which are copolymerizable with epoxy functional hydrido siloxanes under the polymerization conditions to modify the product copolymer. Suitable alkenyl functional compounds include alkenyl functional organic compounds, such as, for example, hexadiene, and alkenyl functional silicone compounds, such as for example, vinyl polydimethylsiloxanes. For example, an alkenyl-functional compound may conveniently be added via hydrosilylation in those embodiments in which the cationic reaction conditions for reacting the epoxide groups are generated using platinum and a hydrido-substituted siloxane, as described above.

The silicone composition may be further processed under low to high shear to adjust the viscosity and sensory feel of the composition. This may be achieved, for example, by subjecting the composition to a moderate to high shearing force. High shear may be applied using, for example, a Sonolator apparatus, a Gaulin Homogenizer or a Micro Fluidizer apparatus. Optionally, one or more fluids may be added to the silicone composition prior to the shearing.

In a preferred embodiment, the silicone composition of the present invention is a solid, typically having a creamy consistency, wherein the copolymer network acts as a means for gelling the fluid to reversibly impart characteristics of a solid to the fluid. At rest, the silicone composition exhibits the properties of a solid gel material. The silicone composition of the present invention exhibits high stability and resistance to syneresis, that is, the composition exhibits little or no tendency for fluid to flow from the composition and imparts high stability and syneresis resistance to personal care compositions which include the silicone composition as a component. The high stability and syneresis resistance persists with prolonged aging of such silicone compositions and personal care compositions. However, fluid may be released from the network by subjecting the silicone composition to a shearing force, such as, for example, by rubbing the composition between one's fingers, to provide improved sensory feel characteristic of the fluid component of the silicone material.

Fluids suitable for use as the fluid component of the composition of the present invention are those compounds or mixtures of two or more compounds that are in the liquid state at or near room temperature, for example, from about 20° C. about 50° C., and about one atmosphere pressure, and include, for example, silicone fluids, hydrocarbon fluids, esters, alcohols, fatty alcohols, glycols and organic oils. In a preferred embodiment, the fluid component of the composition of the present invention exhibits a viscosity of below about 1,000 cSt, preferably below about 500 cSt, more preferably below about 250 cSt, and most preferably below 100 cSt, at 25° C.

In a preferred embodiment, the fluid component of the present invention comprises an emollient compound. Suitable emollient compound include any fluid that provides emollient properties, that is, that when applied to skin, tend to remain on the surface of the skin or in the stratum corneum layer of the skin to act as lubricants, reduce flaking and to improve the appearance of the skin. Emollient compound are generically known and include, for example, hydrocarbons, such as for example, isododecane, isohexadecane and hydrogenated polyisobutene, organic waxes, such as for example, jojoba, silicone fluids, such as, for example, cyclopentasiloxane, dimethicone and bis-phenylpropyl dimethicone, esters, such as, for example, octyldodecyl neopentanoate and oleyl oleate, as well as fatty acids and alcohols, such as for example, oleyl alcohol and isomyristyl alcohol.

In a highly preferred embodiment, the fluid component of the present invention comprises a silicone fluid, more preferably a silicone fluid that exhibits emollient properties, preferably a low molecular weight silicone fluid or alternatively a low molecular weight siloxane compound. Suitable silicone fluids include, for example, cyclic silicones of the formula $D_r$, wherein D, $R^8$ and $R^9$ are as previously defined, preferably with $R^8$ and $R^9$ chosen from the group consisting of monovalent one to six carbon atom monovalent hydrocarbon radicals, more preferably methyl, and r is an integer wherein $3 \leq r \leq 12$, such as, for example, hexamethylcyclotrisiloxane ("$D_3$"), octamethylcyclotetrasiloxane ("$D_4$"), decamethylcyclopentasiloxane ("$D_5$"), and dodecamethylcyclohexasiloxane ("$D_6$") as well as linear or branched organopolysiloxanes having the formula:

wherein:
M' is $R^{19}_3SiO_{1/2}$;
D' is $R^{20}_2SiO_{2/2}$;
T' is $R^{21}SiO_{3/2}$ $R^{19}$, $R^{20}$ and $R^{21}$ are each independently alkyl, aryl or aralkyl containing from one to sixty carbon atoms;

q and s are each independently integers from 0 to 300, preferably from 0 to 100, more preferably from 0 to 50, and most preferably from 0 to 20.

In a preferred embodiment, the silicone composition of the present invention comprises, per 100 parts by weight ("pbw") of the silicone composition, from 0.1 to 99 pbw, more preferably from 0.5 pbw to 30 pbw and still more preferably from 1 to 15 pbw of the polyether siloxane copolymer network and from 1 pbw to 99.9 pbw, more preferably from 70 pbw to 99.5 pbw, and still more preferably from 85 pbw to 99 pbw of the fluid.

The polyether siloxane copolymer network compositions of the present invention may be utilized as prepared or as the silicone component in emulsions. As is generally known, emulsions comprise at least two immiscible phases one of which is continuous and the other which is discontinuous. Further emulsions may be liquids with varying viscosities or solids. Additionally the particle size of the emulsions may be render them microemulsions and when sufficiently small microemulsions may be transparent. Further it is also possible to prepare emulsions of emulsions and these are generally known as multiple emulsions. These emulsions may be:

1) aqueous emulsions where the discontinuous phase comprises water and the continuous phase comprises the polyether siloxane copolymer network of the present invention;

2) aqueous emulsions where the discontinuous phase comprises the polyether siloxane copolymer network of the present invention and the continuous phase comprises water;

3) non-aqueous emulsions where the discontinuous phase comprises a non-aqueous hydroxylic solvent and the continuous phase comprises the polyether siloxane copolymer network of the present invention; and 4) non-aqueous emulsions where the continuous phase comprises a non-aqueous hydroxylic organic solvent and the discontinuous phase comprises the polyether siloxane copolymer network of the present invention.

Non-aqueous emulsions comprising a silicone phase are described in U.S. Pat. No. 6,060,546 and co-pending application U.S. Ser. No. 09/033,788 filed Mar. 3, 1998 the disclosures of which are herewith and hereby specifically incorporated by reference.

As used herein the term "non-aqueous hydroxylic organic compound" means hydroxyl containing organic compounds exemplified by alcohols, glycols, polyhydric alcohols and polymeric glycols and mixtures thereof that are liquid at room temperature, e.g. about 25° C., and about one atmosphere pressure. The non-aqueous organic hydroxylic solvents are selected from the group consisting of hydroxyl containing organic compounds comprising alcohols, glycols, polyhydric alcohols and polymeric glycols and mixtures thereof that are liquid at room temperature, e.g. about 25° C., and about one atmosphere pressure. Preferably the non-aqueous hydroxylic organic solvent is selected from the group consisting of ethylene glycol, ethanol, propyl alcohol, iso-propyl alcohol, propylene glycol, dipropylene glycol, tripropylene glycol, butylene glycol, iso-butylene glycol, methyl propane diol, glycerin, sorbitol, polyethylene glycol, polypropylene glycol mono alkyl ethers, polyoxyalkylene copolymers and mixtures thereof.

Once the desired form is attained whether as a silicone only phase, an anhydrous mixture comprising the silicone phase, a hydrous mixture comprising the silicone phase, a water-in-oil emulsion, an oil-in-water emulsion, or either of the two non-aqueous emulsions or variations thereon, the resulting material is usually a high viscosity cream with good feel characteristics, and high absorbance of volatile siloxanes. It is capable of being blended into formulations for hair care, skin care, antiperspirants, sunscreens, cosmetics, color cosmetics, insect repellants, vitamin and hormone carriers, fragrance carriers and the like.

The personal care applications where the polyether siloxane copolymer network of the present invention and the silicone compositions derived therefrom of the present invention may be employed include, but are not limited to, deodorants, antiperspirants, antiperspirant/deodorants, shaving products, skin lotions, moisturizers, toners, bath products, cleansing products, hair care products such as shampoos, conditioners, mousses, styling gels, hair sprays, hair dyes, hair color products, hair bleaches, waving products, hair straighteners, manicure products such as nail polish, nail polish remover, nails creams and lotions, cuticle softeners, protective creams such as sunscreen, insect repellent and anti-aging products, color cosmetics such as lipsticks, foundations, face powders, eye liners, eye shadows, blushes, makeup, mascaras and other personal care formulations where silicone components have been conventionally added, as well as drug delivery systems for topical application of medicinal compositions that are to be applied to the skin.

In a preferred embodiment, the personal care composition of the present invention further comprises one or more personal care ingredients. Suitable personal care ingredients include, for example, emollients, moisturizers, humectants, pigments, including pearlescent pigments such as, for example, bismuth oxychloride and titanium dioxide coated mica, colorants, fragrances, biocides, preservatives, antioxidants, anti-microbial agents, anti-fungal agents, antiperspirant agents, exfoliants, hormones, enzymes, medicinal compounds, vitamins, salts, electrolytes, alcohols, polyols, absorbing agents for ultraviolet radiation, botanical extracts, surfactants, silicone oils, organic oils, waxes, film formers, thickening agents such as, for example, fumed silica or hydrated silica, particulate fillers, such as for example, talc, kaolin, starch, modified starch, mica, nylon, clays, such as, for example, bentonite and organo-modified clays.

Suitable personal care compositions are made by combining, in a manner known in the art, such as, for example, by mixing, one or more of the above components with the polyether siloxane copolymer network, preferably in the form of the silicone composition of the present invention. Suitable personal care compositions may be in the form of a single phase or in the form of an emulsion, including oil-in-water, water-in-oil and anhydrous emulsions where the silicone phase may be either the discontinuous phase or the continuous phase, as well as multiple emulsions, such as, for example, oil-in water-in-oil emulsions and water-in-oil-in water-emulsions.

In one useful embodiment, an antiperspirant composition comprises the polyether siloxane copolymer network of the present invention and one or more active antiperspirant agents. Suitable antiperspirant agents include, for example, the Category I active antiperspirant ingredients listed in the U.S. Food and Drug Administration's Oct. 10, 1993 Monograph on antiperspirant drug products for over-the-counter human use, such as, for example, aluminum halides, aluminum hydroxyhalides, for example, aluminum chlorohydrate, and complexes or mixtures thereof with zirconyl oxyhalides and zirconyl hydroxyhalides, such as for example, aluminum-zirconium chlorohydrate, aluminum zirconium glycine complexes, such as, for example, aluminum zirconium tetrachlorohydrex gly.

In another useful embodiment, a skin care composition comprises the polyether siloxane copolymer network, preferably in the form of silicone composition of the present invention, and a vehicle, such as, for example, a silicone oil or an organic oil. The skin care composition may, optionally, further include emollients, such as, for example, triglyceride esters, wax esters, alkyl or alkenyl esters of fatty acids or polyhydric alcohol esters and one or more the known components conventionally used in skin care compositions, such as, for example, pigments, vitamins, such as, for example, Vitamin A, Vitamin C and Vitamin E, sunscreen or sunblock compounds, such as, for example, titanium dioxide, zinc oxide, oxybenzone, octylmethoxy cinnamate, butylmethoxy dibenzoylm ethane, p-aminobenzoic acid and octyl dimethyl-p-aminobenzoic acid.

In another useful embodiment, a color cosmetic composition, such as, for example, a lipstick, a makeup or a mascara composition comprises the polyether siloxane copolymer network, preferably in the form of silicone composition of the present invention, and a coloring agent, such as a pigment, a water soluble dye or a liposoluble dye.

In another useful embodiment, the compositions of the present invention are utilized in conjunction with fragrant materials. These fragrant materials may be fragrant compounds, encapsulated fragrant compounds, or fragrance releasing compounds that either the neat compounds or are encapsulated. Particularly compatible with the compositions of the present invention are the fragrance releasing silicon containing compounds as disclosed in U.S. Pat. Nos. 6,046, 156; 6,054,547; 6,075,111; 6,077,923; 6,083,901; and 6,153, 578; all of which are herein and herewith specifically incorporated by reference.

The uses of the compositions of the present invention are not restricted to personal care compositions, other products such as waxes, polishes and textiles treated with the compositions of the present invention are also contemplated.

Experimental Preparation of Polyether Siloxane Copolymer Network Compositions

Preparation Example 1. 494.5 g of a hydride fluid with approximate composition $M^H D_{300} D^H_4 M^H$ was mixed with 5.5 g of vinyl cyclohexene oxide, 1500 g of decamethyl cyclopentasiloxane (D5), and 0.1 g of a platinum divinyltetramethyldisiloxane catalyst solution. The result was heated to 80° C. After a couple of hours, an additional portion of platinum catalyst solution was added. The material was heated for a total of 4 hours at 80° C. In this way a gel material ExpMJO-07-391 was obtained with a solids content of about 26%. 567 g of ExpMJO-07-391 was then mixed with 1433 g of additional D5. Then the result was passed twice through a Gaulin homogenizer at 4500 psi. The result, ExpMJO-07-401 had a solids content of about 7.3% and a viscosity of 24,200 cps. This material gave a very silky feel when rubbed on the skin.

Preparation Example 2. 300 g of a hydride fluid with approximate composition $M^H D_{337} D^H_{118} M^H$ was mixed with 3.94 g of vinyl cyclohexene oxide, 37 g of Gulftene C30+ Alpha Olefin Fraction from Chevron (herein defined when a substituent as C30+), 1022.8 g of decamethyl cyclopentasiloxane (D5), and 0.1 g of a platinum divinyltetramethyldisiloxane catalyst solution. The result was heated to 80° C. for 8 hours producing ExpMJO-07-433. This material had a solids content of about 25.5%. 587.5 g of ExpMJO-07-433 was then swollen with 1412.5 g of additional D5 and then passed through a Gaulin homogenizer at 4500 psi. The result, ExpMJO-07-434, had a solids content of about 7.4% and a viscosity of 45,000 cps. It also gave a silky feel when rubbed on the skin.

Preparation Example 3. 300 g of a hydride fluid with approximate composition $M^H_{1.73} D_{388} D^H_{6.9} M_{0.27}$ was mixed with 3.00 g of vinyl cyclohexene oxide, 9 g of Gulftene C30+ Alpha Olefin Fraction from Chevron, 936 g of decamethyl cyclopentasiloxane (D5), and 0.1 g of a platinum divinyltetramethyldisiloxane catalyst solution. The result was heated to 80° C. for 8 hours producing ExpMJO-07-422. This material had a solids content of about 25.7%. 591.4 g of ExpMJO-07-422 was then swollen with 1408.6 g of additional D5 and then passed through a Gaulin homogenizer at 4500 psi. The result, ExpMJO-07-437, had a solids content of about 7.26% and a viscosity of 39,000 cps.

Preparation Example 4. 300 g of a hydride fluid with approximate composition $M^H_{1.73} D_{388} D^H_{6.9} M_{0.27}$ was mixed with 3.00 g of vinyl cyclohexene oxide, 3 g of a C-16/18 Alpha Olefin Fraction, 918 g of decamethyl cyclopentasiloxane (D5), and 0.1 g of a platinum divinyltetramethyldisiloxane catalyst solution. The result was heated to 80° C. for 8 hours producing ExpMJO-07-424. This material had a solids content of about 25.7%. 591.4 g of ExpMJO-07-424 was then swollen with 1408.6 g of additional D5 and then passed through a Gaulin homogenizer at 4500 psi. The result, ExpMJO-07-438, had a solids content of about 7.57% and a viscosity of 39,500 cps.

Preparation Example 5. 300 g of a hydride fluid with approximate composition $M^H D_{337} D^H_{11.8} M^H$ was mixed with 4.89 g of vinyl cyclohexene oxide, 26.4 g of Gulftene C30+ Alpha Olefin Fraction from Chevron, 733 g of decamethyl cyclopentasiloxane (D5), and 0.08 g of a platinum divinyltetramethyldisiloxane catalyst solution. The result was heated to 80° C. for 6 hours producing ExpMJO-07-464. This material had a solids content of about 30.84%. 533 g of ExpMJO-07-

464 was then swollen with 967 g of additional D5 and then passed through a Gaulin homogenizer at 4500 psi. The result, ExpMJO-07-465, had a solids content of about 11% and a viscosity of 200,000 cps.

Preparation Example 6. 300 g of a hydride fluid with approximate composition $MD_{100}D^H_{10.5}M$ was mixed with 13.53 g of vinyl cyclohexene oxide, 34.84 g of Gulftene C30+ Alpha Olefin Fraction from Chevron, 647 g of decamethyl cyclopentasiloxane (D5), and 0.10 g of a platinum divinyltetramethyldisiloxane catalyst solution. The result was heated to 80° C. for 6 hours producing ExpMJO-07-477. This material had a solids content of about 35.25%. 533 g of ExpMJO-07-464 was then swollen with 947 g of additional D5 and then passed through a Gaulin homogenizer at 4500 psi. The result, ExpMJO-07-482, had a solids content of about 12.69% and a viscosity of 16,500 cps.

Preparation Example 7. 316.4 g of a hydride fluid with approximate composition $M^H D_{200} D^H_{10.5} M^H$ was mixed with 7.56 g of vinyl cyclohexene oxide 7.00 g of 4-allyl-2-methoxy-phenol, 840 g of decamethyl cyclopentasiloxane (D5), and 0.09 g of a platinum divinyltetramethyldisiloxane catalyst solution. The result was heated to 80° C. for 6 hours producing ExpMJO-08-537. 418 g of ExpMJO-08-537 was then swollen with 582 g of additional D5 and then passed through a Gaulin homogenizer at 8000 psi. The result, ExpMJO-08-540, had a solids content of about 12% and a viscosity of 198,000 cps.

Preparation Example 8. Example Showing Gelation Followed by Hydrosilyation. 300 g of a hydride fluid with approximate composition $M^H D_{337} D^H_{11.8} M^H$ was mixed with 3.94 g of vinyl cyclohexene oxide, 905.4 g of decamethyl cyclopentasiloxane (D5), and 0.1 g of a platinum divinyltetramethyl disiloxane catalyst solution. The result was heated to 80° C. for 4 hours with good mixing. A small sample of the gelled reaction mixture was taken out and analyzed by FTIR. This clearly showed that there was residual SiH remaining. Next, a mixture of 30 g of the di isostearic acid ester of trimethylolpropane monoallyl ether, 100 g of D5 and 1 drop of Pt catalyst was added. The result was heated for another 2 hours at 80° C. At this end of this time a gel was obtained (Gel E) which had a solids content of 25.1%. FTIR analysis showed that the size of the SiH stretch (ca. 2140 cm−1) had substantially decreased.

Preparation Example 9. Example Showing Addition of a Concentrated Hydridosiloxane. 300 g of a hydride fluid with approximate composition $M^H_{1.73} D_{388} D^H_{6.9} M_{0.27}$ was mixed with 3.00 g of vinyl cyclohexene oxide, 4.00 g of 4-allyl-2-methoxy-phenol, 20.8 g of Gulftene C30+ Alpha Olefin Fraction from Chevron, 984 g of decamethyl cyclopentasiloxane (D5), and 0.1 g of a platinum divinyltetramethyl disiloxane catalyst solution. The result was heated to 80° C. for an hour with good mixing. At this point, a mixture of 4 g of a trimethylsilyl stopped methyl hydrogen polsiloxane and 5 g decamethyl cyclopentasiloxane was added. With 3 minutes, the reaction mixture gelled. Heating was continued for 5 hours in order to ensure complete reaction.

Preparation Example 10 300 g of a hydride fluid with approximate composition $M^H D_{200} D^H_{10.5} M^H$ was mixed with 7.22 g of vinyl cyclohexene oxide, 34.1 g of Gulftene C30+ Alpha Olefin Fraction from Chevron, 796 g of decamethyl cyclopentasiloxane (D5), and 0.085 g of a platinum divinyltetramethyldisiloxane catalyst solution. The result was heated to 80° C. for 6 hours producing ExpMJO-07-481. 562 g of ExpMJO-07-481 was then swollen with a mixture of 938 g of additional D5 and 1.0 g of a 10% solution of methyl di(hydrogenated tallow)amine in Isopar C and then passed through a Gaulin homogenizer at 4500 psi. The result, ExpMJO-07-484, had a solids content of about 11.58% and a viscosity of 85,000 cps.

Experimental Preparation of Cosmetic Compositions Using Polyether Siloxane Copolymer Network Compositions

COSMETIC EXAMPLE 1

| Composition | wt % A(Control) | wt % B(Ex1) |
|---|---|---|
| Stearyl alcohol | 15 | 15 |
| Hydrogenated castor oil | 5 | 5 |
| Isododecane | 10 | 10 |
| SF1202 | 45 | 35 |
| Talc | 1 | 1 |
| Al Zr Trichlorohydrex Gly | 24 | 24 |
| ExpMJO-07-465 | 0 | 10 |

These antiperspirant sticks were made by heating stearyl alcohol, hydrogenated castor oil, isododecane, SF1202 and ExpMJO-07-465 until the gellants were melted. Al Zr Trichlorohydrex gly was added to the batch at 70° C. and mixed until uniform. Antiperspirants were poured to containers at about 60° C. The antiperspirant was evaluated for whiteness, ability to hold liquid, feel, and hardness of the stick. The whiteness was determined by applying antiperspirant onto dark color vinyl slides to mimic the consumer application methods. Vinyl test slides were air dried for 15 min and the whiteness was determined by appearance. The control antiperspirants showed intense whiteness within 5-10 min after application. The antiperspirant B showed whiteness reduction as compared to control. Antiperspirant B also demonstrated a superior ability to hold cosmetic fluid when using thumb pressure was applied to the sticks. It also improved the rigidity and resiliency of the stick in this formulation. In addition, it provided lubricious skin feel with powdery finish. Formulation B also modified the crystallization of organic gelling agents by providing a better and more uniform matrix and reducing the growth of stearyl alcohol crystallization matrix.

COSMETIC EXAMPLE 2

| Composition | A wt % | B(Ex2) wt % |
|---|---|---|
| Part A | | |
| Propylene glycol | 42.2 | 42.2 |
| Hydroxypropyl cellulose | 0.5 | 0.5 |
| DBS | 2 | 2 |
| Part B | | |
| 30% AlZr Pentachlorohydrex gly in propylene glycol | 30 | 30 |
| Part C | | |
| SF1202 | 10 | 0 |
| ExpMJO-07-465 | 0 | 10 |
| SF1555 | 15 | 15 |
| 40% Dimethicone copolyol in D5 | 0.3 | 0.3 |

These clear antiperspirant sticks were prepared by heating propylene glycol to 80° C. and slowly sprinkling in hydroxypropyl cellulose(HPC). After the HPC was uniformly dispersed, the mixture was heated up to 130° C. and DBS was added to the batch. The glycol mixture was cooled down to 100° C. when a solution of the antiperspirant active was added. The silicone phase or part C was separately mixed and heated to 80° C. and then the glycol phase was slowly introduced to the silicone phase.

The clear antiperspirant B in this invention showed no syneresis and increased stiffness of the stick compared to control. It gave good pay-out and smooth uniform deposition of antiperspirant active on the skin when compared to control.

Cosmetic Example 3 and 4 with a powdery finish appearance. The foundation B in this invention had improved stability after one week at room temperature compared to the formulation A(control) which showed syneresis at the same time.

Formulation D gave the similar benefits as described in formulation B. In addition, it also provided wash off resistance which made personal care products more durable to perspiration or during swimming. Formulation D had an ability to control shine as shown in the result above.

| Ingredients | A Wt % | B(Ex3) Wt % | C Wt % | D(Ex4) Wt % |
|---|---|---|---|---|
| Part A | | | | |
| SF1202 | 21.65 | 11.65 | 19.2 | 9.9 |
| Isododecane | 8.7 | 8.7 | | |
| Caprylic/capric Triglyceride | 3.6 | 3.6 | | |
| Dimethicone | | | 9.3 | 9.3 |
| Phenyl trimethicone | | | 9.3 | 9.3 |
| Sorbitan oleate | 1.5 | 1.5 | 1.4 | 1.4 |
| 40% Dimethicone copolyol in D5 | 3.75 | 3.75 | 3.5 | 3.5 |
| ExpMJO-07-465 | | 10 | | |
| ExpMJO-07-434 | | | | 9.3 |
| Part B | | | | |
| Iron oxides(red, yellow, black) | 2.34 | 2.34 | 2.18 | 2.18 |
| $TiO_2$ | 8.73 | 8.73 | 8.11 | 8.11 |
| 10% Dimethicone copolyol in D5 | 6.63 | 6.63 | 6.15 | 6.15 |
| Part C | | | | |
| Deionized water | 37.75 | 37.75 | 34.98 | 34.98 |
| Butylene glycol | 5 | 5 | 4.65 | 4.65 |
| Xanthan gum | 0.1 | 0.1 | 0.1 | 0.1 |
| $C_{11-15}$ Pareth-7 | 0.25 | 0.25 | 0.23 | 0.23 |
| Magnesium sulfate | | | 0.9 | 0.9 |

| Parameter | Foundation A | Foundation B(Ex3) | Foundation C | Foundation D(Ex4) |
|---|---|---|---|---|
| Degree of coverage[1] | — | Excellent | — | Excellent |
| Gloss | 3.2 | 3.2 | 17.2 | 11.6 |
| Appearance after 5 cycles of wash off[2] | NA | NA | Washed away | Partially washed away, the remaining foundation showed powdery finish. |

Note:
[1] Degree of coverage was conducted against the control. Formulation A was the control of formulation B and formulation C was the control of formulation D.
[2] Formulation C and D was tested for appearance of foundation coated on vinyl slides after 5 cycles of wash off. The wash off resistance method was described in ASTM D1913.

The foundations were prepared by mixing part A and part B together at room temperature until uniform. The emulsion was developed when the water phase (Part C) was added into the oil phase. The foundation samples were evaluated for coverage on vinyl slides at 24 micron in thickness. All foundations were evaluated on ease of spreadability during draw down, appearance, degree of coverage and shine. Shine was determined by using gloss meter after 12 hours. In this study formulation B was evaluated against formulation A(control) and formulation D was evaluated against formulation C(control).

Formulation B gave superior uniform coverage by reducing the appearance of lines and imperfections on the vinyl slides, and by reducing shine during initial rub-out. However, both formulation A and B did not show the difference in gloss after 12 hours. Formulation B imparted a luxurious silky feel Cosmetic Example 5 and 6

These two examples were prepared to illustrate organic compatibility of silicone gel in this invention and compared it with the current elastomer gel with an INCI name of cyclopentasiloxane (and) dimethicone/vinyl dimethicone crosspolymer (SFE839).

Cosmetic Example 5

| Composition | Appearance |
|---|---|
| 25% Petrolatum in SFE839 | fluid |
| 25% Petrolatum in ExpMJO-07-465 | gel |

When petrolatum was mixed with SFE839, the formulation lost the structure and became an opaque fluid mixture. This suggested the incompatibility of petrolatum and SFE839. On the other hand, when petrolatum was incorporated into the gel of this invention, the gel had an ability to maintain product integrity, indicating the compatibility of this gel and petrolatum.

Cosmetic Example 6

| Composition | Appearance |
| --- | --- |
| 50% Cetearyl methicone in SFE839 | Incompatible |
| 50% Cetearyl methicone in ExpMJO-07-465 | Compatible |

Cetearyl methicone is a linear alkyl substituted silicone and it provides moisturization to the formulation by creating an occlusive barrier on the skin. When this silicone moisturizer was combined with the new gel, it showed good compatibility whereas the SFE839 did not. In addition, the gel according to this invention is easier to blend with cosmetic ingredients in that it does not require the high shear mixer or lengthy mixing time required by SFE839.

Cosmetic Example 7

This skin treatment gel was prepared by combining all ingredients listed below until uniform at room temperature. The gel was used as delivery system for skin treatment and it is suitable for both heat sensitive and non-heat sensitive active ingredients since it does not require heating during manufacturing. The absence of water in this formulation ensures the efficacy of vitamin C until used.

| Composition | wt % |
| --- | --- |
| Polymethylsilsesquioxane(Tospearl2000B) | 0.5 |
| Vitamin C | 1 |
| Hydrogenated polydecene | 10 |
| ExpMJO-07-434 | 88.5 |

Cosmetic Example 8

A lip treatment comprising ingredients below is useful for contouring, durability and moisturization feel.

| Composition | wt % |
| --- | --- |
| ExpMJO-07-465 | 89 |
| Phenylpropyldimethylsiloxysilicate | 10 |
| Nylon-12 | 1 |

Cosmetic Example 9

Silky body lotion is made by combining part A together and heating to 80° C. In a separate vessel, part B is mixed and heated to 75° C. The emulsion is formed when part A and part B are added together under high shear mixing. This lotion provides light and lubricious skin feel.

| Composition | wt % |
| --- | --- |
| Part A | |
| ExpMJO-07-465 | 10 |
| Caprylic/capric triglyceride | 5 |
| $C_{30-45}$ Alkyl Dimethicone | 5 |
| Glyceryl stearate (and) PEG-100 stearate | 4 |
| Part B | |
| Water | q.s. |
| Xanthan gum | 0.1 |
| Glycerin | 2 |
| Preservatives, color, fragrance | 1 |

Cosmetic Examples 10-13

Water resistant lotions useful for various personal care products were prepared by combining part A and part B together at room temperature. The lotions were then applied on glass slides and tested for degree of water resistance using the method described in ASTM D1913. The degree of wash off resistance is the numbers of wash off cycles taken before the lotion was completely washed away. The body lotion B-E with the new gel in this invention showed water resistant benefit as shown below.

| | Composition | | | | |
| --- | --- | --- | --- | --- | --- |
| | A | B | C | D | E |
| | Cosmetic Examples | | | | |
| | Control wt % | 10 wt % | 11 wt % | 12 wt % | 13 wt % |
| Part A | | | | | |
| Sorbitan oleate | 0.6 | 0.6 | 0.6 | 0.6 | 0.6 |
| 10% Dimthicone copolyol in D5 | 10 | 10 | 10 | 10 | 10 |
| SF1202 | 16 | 4 | 4 | 4 | 4 |
| ExpMJO-07-401 | 0 | 12 | 0 | 0 | 0 |
| ExpMJO-07-437 | 0 | 0 | 12 | 0 | 0 |
| ExpMJO-07-434 | 0 | 0 | 0 | 12 | 0 |
| ExpMJO-07-438 | 0 | 0 | 0 | 0 | 12 |
| Part B | | | | | |
| Glycerin | 1 | 1 | 1 | 1 | 1 |
| Sodium chloride | 1 | 1 | 1 | 1 | 1 |
| Quaternium-15 | 0.1 | 0.1 | 0.1 | 0.1 | 0.1 |
| Water | q.s. | q.s. | q.s. | q.s. | q.s. |

Wash off resistant result

| Formulation | Cycles of wash off |
| --- | --- |
| A(control) | 5 |
| B | 15 |
| C | 15 |
| D | 15 |
| E | 10 |

Cosmetic Example 14

Hair shampoo comprising ingredients below gives a silky feel to hair fibers. This shampoo can be prepared into 2 ways;

one is directly add silicone gel to the shampoo, and the other is pre-blend silicone gel with at least one surfactant and water until emulsion developed and add silicone gel emulsion to the shampoo.

This shampoo is made by mixing ingredients as ordered.

| Compositions | wt % |
| --- | --- |
| Ammonium lauryl sulfate | 35 |
| Cocamidopropyl betaine | 5 |
| Water | 56.6 |
| Preservative | 0.01 |
| Acrylate/C$_{10-30}$ alkyl acrylate crosspolymer | 0.8 |
| Sodium hydroxide | adjust to pH 7.5 |
| ExpMJO-07-465 | 2.5 |
| Citric acid | adjust to pH 6 |

Cosmetic Example 15

This hair conditioner for daily use provides softness, lubricity and body.

| Composition | wt % |
| --- | --- |
| Deionized water | 93 |
| Hydroxyethylcellulose | 1.5 |
| Silicone gel emulsion | 2 |
| Cetrimonium chloride | 3 |
| Preservatives, color, fragrance | q.s. |

Cosmetic Example 16

The leave on hair conditioner reduces fly-away and increases body and volume.

| Composition | wt % |
| --- | --- |
| ExpMJO-07-465 | 50 |
| Dimethicone copolyol | 5 |
| Isododecane | 45 |

Cosmetic Example 17

This soft solid antiperspirant contains silicone gel an antisyneresis, thickening and sensory enhancer. The gel shows excellent organic compatibility. It is used in combination with an organic thickener to achieve the desired texture and rigidity.

| Ingredient | Part/Wt (%) |
| --- | --- |
| Cyclopentasiloxane (SF1202) | 37.0 |
| Dimethicone (SF96-10) | 8.0 |
| C12-15 Alkyl Benzoate | 8.0 |
| Hydrogenated Castor Oil (mp 70° C.) | 7.0 |
| C18-36 Acid Triglyceride | 7.0 |
| ExpMJO-07-484 | 5.0 |
| Talc | 3.0 |
| Aluminum Zirconium Tetrachlorohydrex Gly | 25.0 |

Cosmetic Example 18

This silicone lipstick contains silicone gel to soften lips. There are two silicones, SF1528, and Exp-MJO-07-484, which give a unique soft silky feel. Sunscreens could be added to the formulations for solar protection.

| Ingredient | Part/Wt (%) |
| --- | --- |
| Cyclopentasiloxane (and) PEG/PPG-20/15 Dimethicone (SF1528) | 20.0 |
| ExpMJO-07-484 | 40.0 |
| C18-36 Acid Triglyceride | 5.0 |
| Ozokerite | 3.0 |
| Polyethylene | 5.0 |
| Isododecane | 20.0 |
| D&C Red No. 7 Ca Lake | 7.0 |

Materials listed as SFxxxx are commercially available silicone materials available from GE Silicones, 260 Hudson River Road, Waterford N.Y. 12188.

These examples are to be construed as exemplary in nature only and are not intended in any way to limit the appended claims. It is contemplated that a person having ordinary skill in the art would be able to produce obvious variations of the subject matter and disclosures herein contained that would be by reason of such ordinary skill within the literal or equitable scope of the appended claims.

Having described the invention that which is claimed is:

1. A composition comprising the reaction product of:

$$M_a M^H_b M^E_c D_d D^H_e D^E_f T_g T^H_h T^E_i Q_j$$

where
$M = R^1 R^2 R^3 SiO_{1/2}$;
$M^H = R^4 R^5 HSiO_{1/2}$;
$M^E = R^6 R^7 R^E SiO_{1/2}$;
$D = R^8 R^9 SiO_{1/2}$;
$D^H = R^{10} HSiO_{2/2}$;
$D^E = R^{11} R^E SiO_{2/2}$;
$T = R^{12} SiO_{3/2}$;
$T^H = HSiO_{3/2}$;
$T^E = R^E SiO_{3/2}$; and
$Q = SiO_{4/2}$;
where $R^1$, $R^2$, $R^3$, $R^8$, $R^9$ and $R^{12}$ are independently monovalent hydrocarbon radicals having from one to sixty carbon atoms; $R^4$, $R^5$ and $R^{10}$ are independently monovalent hydrocarbon radicals having from one to sixty carbon atoms or hydrogen; $R^6$, $R^7$, $R^{11}$ are independently monovalent hydrocarbon radicals having from one to sixty carbon atoms or $R^E$; each $R^E$ is independently a monovalent hydrocarbon radical containing one or more oxirane moieties having from one to sixty carbon atoms; the stoichiometric subscripts a, b, c, d, e, f, g, h, i, and j are either zero or positive subject to the following limitations: a+b+c>1; b+e+h>1; c+f+i>1; b+e+h>c+f+i; wherein said composition having an original volume may be swollen by a low molecular weight silicone fluid from 2 to 1,000 times its original volume.

2. The composition of claim 1 where $R^E$ has the formula:

$$\begin{array}{c} R^{18} \; H \\ | \quad | \\ -C-C-Q_n-Q_m \\ | \quad | \\ R^{17} \; R^{16} \end{array} \begin{array}{c} R^{15} \quad R^{14} \\ \diagup \\ \diagdown O \diagup R^{13} \end{array}$$

where $R^{13}$, $R^{14}$, $R^{15}$, $R^{16}$, $R^{17}$ and $R^{18}$ are each independently selected from the group of hydrogen and monovalent hydrocarbon radicals having from one to sixty carbon atoms, $Q_n$ is a di- or trivalent hydrocarbon radical having from one to sixty carbon atoms, $Q_m$ is a divalent hydrocarbon radical having from one to sixty carbon atoms with the subscripts m and n independently zero or one subject to the limitation that when Qm is trivalent one of $R^{13}$ or $R^{14}$ is absent.

3. The composition of claim 1 where $R^E$ is obtained by hydrosilylation of a compound selected from the group consisting of 4-vinyl cyclohexene oxide, allyl glycidyl ether, limonene oxide, 1,2-epoxy-5-hexene, 1,2-epoxy-7-octene, norbornadiene monoepoxide and 1,2-epoxy-9-decene.

4. The composition of claim 2 where $R^{13}$, $R^{14}$, $R^{15}$, $R^{16}$, $R^{17}$ and $R^{18}$ are hydrogen and m and n are zero.

5. The composition of claim 3 where $R^E$ is obtained by hydrosilylation of 4-vinyl cyclohexene oxide.

6. The composition of claim 1 where $R^1$, $R^2$, $R^3$, $R^8$, $R^9$ and $R^{12}$ are independently selected from the group consisting of methyl, ethyl, sec-butyl, tert-butyl, octyl, decyl, dodecyl, cetyl, stearyl, ethenyl, propenyl, butynyl, hydroxypropyl, butoxy, 2,5,8-trioxadecanyl, carboxymethyl, chloromethyl, C30+ and 3,3,3-fluoropropyl.

7. The composition of claim 2 where $R^1$, $R^2$, $R^3$, $R^8$, $R^9$ and $R^{12}$ are independently selected from the group consisting of methyl, ethyl, sec-butyl, tert-butyl, octyl, decyl, dodecyl, cetyl, stearyl, ethenyl, propenyl, butynyl, hydroxypropyl, cyanoethyl, butoxy, 2,5,8-trioxadecanyl, carboxymethyl, chloromethyl and 3,3,3-fluoropropyl.

8. The composition of claim 3 where $R^1$, $R^2$, $R^3$, $R^8$, $R^9$ and $R^{12}$ are independently selected from the group consisting of methyl, ethyl, sec-butyl, tert-butyl, octyl, decyl, dodecyl, cetyl, stearyl, ethenyl, propenyl, butynyl, hydroxypropyl, cyanoethyl, butoxy, 2,5,8-trioxadecanyl, carboxymethyl, chloromethyl and 3,3,3-fluoropropyl.

9. The composition of claim 4 where $R^1$, $R^2$, $R^3$, $R^8$, $R^9$ and $R^{12}$ are independently selected from the group consisting of methyl, ethyl, sec-butyl, tert-butyl, octyl, decyl, dodecyl, cetyl, stearyl, ethenyl, propenyl, butynyl, hydroxypropyl, cyanoethyl, butoxy, 2,5,8-trioxadecanyl, carboxymethyl, chloromethyl and 3,3,3-fluoropropyl.

10. The composition of claim 5 where $R^1$, $R^2$, $R^3$, $R^8$, $R^9$ and $R^{12}$ are independently selected from the group consisting of methyl, ethyl, sec-butyl, tert-butyl, octyl, decyl, dodecyl, cetyl, stearyl, ethenyl, propenyl, butynyl, hydroxypropyl, cyanoethyl, butoxy, 2,5,8-trioxadecanyl, carboxymethyl, chloromethyl and 3,3,3-fluoropropyl.

11. An aqueous emulsion where the discontinuous phase comprises water and the continuous phase comprises a composition comprising the reaction product of:

$$M_a M^H_b M^E_c D_d D^H_e D^E_f T_g T^H_h T^E_i Q_j$$

where
$M=R^1R^2R^3SiO_{1/2}$;
$M^H=R^4R^5HSiO_{1/2}$;
$M^E=R^6R^7R^ESiO_{1/2}$;
$D=R^8R^9SiO_{2/2}$;
$D^H=R^{10}HSiO_{2/2}$;
$D^E=R^{11}R^ESiO_{2/2}$;
$T=R^{12}SiO_{3/2}$;
$T^H=HSiO_{3/2}$;
$T^E=R^ESiO_{3/2}$; and
$Q\ SiO_{4/2}$;
where $R^1$, $R^2$, $R^3$, $R^8$, $R^9$ and $R^{12}$ are independently monovalent hydrocarbon radicals having from one to sixty carbon atoms; $R^4$, $R^5$ and $R^{10}$ are independently monovalent hydrocarbon radicals having from one to sixty carbon atoms or hydrogen; $R^6$, $R^7$, $R^{11}$ are independently monovalent hydrocarbon radicals having from one to sixty carbon atoms or $R^E$;

each $R^E$ is independently a monovalent hydrocarbon radical containing one or more oxirane moieties having from one to sixty carbon atoms; the stoichiometric subscripts a, b, c, d, e, f, g, h, i and j are either zero or positive subject to the following limitations: a+b+c>1; b+e+h>1; c+f+i>1; b+e+h>c+f+i.

12. The composition of claim 11 where $R^E$ has the formula:

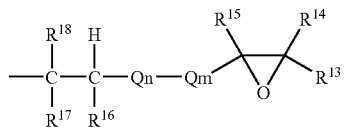

where $R^{13}$, $R^{14}$, $R^5$, $R^{16}$, $R^{17}$ and $R^{18}$ are each independently selected from the group of hydrogen and monovalent hydrocarbon radicals having from one to sixty carbon atoms, $Q_m$ is a di- or trivalent hydrocarbon radical having from one to sixty carbon atoms, $Q_n$ is a divalent hydrocarbon radical having from one to sixty carbon atoms with the subscripts m and n independently zero or one subject to the limitation that when Qm is trivalent one of $R^{13}$ or $R^{14}$ is absent.

13. The composition of claim 1 where $R^E$ is obtained by hydrosilylation of a compound selected from the group consisting of 4-vinyl cyclohexene oxide, allyl glycidyl ether, limonene oxide, 1,2-epoxy-5-hexene, 1,2-epoxy-7-octene, norbornadiene monoepoxide and 1,2-epoxy-9-decene.

14. The composition of claim 12 where $R^{13}$, $R^{14}$, $R^{15}$, $R^{16}$, $R^{17}$ and $R^{18}$ are hydrogen and m and n are zero.

15. The composition of claim 13 where $R^E$ is obtained by hydrosilylation of 4-vinyl cyclohexene oxide.

16. The composition of claim 11 where $R^1$, $R^2$, $R^3$, $R^8$, $R^9$ and $R^{12}$ are independently selected from the group consisting of methyl, ethyl, sec-butyl, tert-butyl, octyl, decyl, dodecyl, cetyl, stearyl, ethenyl, propenyl, butynyl, hydroxypropyl, cyanoethyl, butoxy, 2,5,8-trioxadecanyl, carboxymethyl, chloromethyl, C30+ and 3,3,3-fluoropropyl.

17. The composition of claim 12 where $R^1$, $R^2$, $R^3$, $R^8$, $R^9$ and $R^{12}$ are independently selected from the group consisting of methyl, ethyl, sec-butyl, tert-butyl, octyl, decyl, dodecyl, cetyl, stearyl, ethenyl, propenyl, butynyl, hydroxypropyl, cyanoethyl, butoxy, 2,5,8-trioxadecanyl, carboxymethyl, chloromethyl and 3,3,3-fluoropropyl.

18. The composition of claim 13 where $R^1$, $R^2$, $R^3$, $R^8$, $R^9$ and $R^{12}$ are independently selected from the group consisting of methyl, ethyl, sec-butyl, tert-butyl, octyl, decyl, dodecyl, cetyl, stearyl, ethenyl, propenyl, butynyl, hydroxypropyl, cyanoethyl, butoxy, 2,5,8-trioxadecanyl, carboxymethyl, chloromethyl and 3,3,3-fluoropropyl.

19. The composition of claim 14 where $R^1$, $R^2$, $R^3$, $R^8$, $R^9$ and $R^{12}$ are independently selected from the group consisting of methyl, ethyl, sec-butyl tert-butyl, octyl, decyl, dodecyl, cetyl, stearyl, ethenyl, propenyl, butynyl, hydroxypropyl, cyanoethyl, butoxy, 2,5,8-trioxadecanyl, carboxymethyl, chloromethyl and 3,3,3-fluoropropyl.

20. The composition of claim 15 where $R^1$, $R^2$, $R^3$, $R^8$, $R^9$ and $R^{22}$ are independently selected from the group consisting of methyl, ethyl, sec-butyl, tert-butyl, octyl, decyl, dodecyl, cetyl, stearyl, ethenyl, propenyl, butynyt, hydroxypropyl, cyanoethyl, butoxy, 2,5,8-trioxadecanyl, carboxymethyl, chloromethyl and 3,3,3-fluoropropyl.

21. An aqueous emulsion where the continuous phase comprises water and the discontinuous phase comprises a composition comprising the reaction product of:

$$M_a M^H_b M^E_c D_d D^H_e D^E_f T_g T^H_h T^E_i Q_j$$

where
M=$R^1R^2R^3SiO_{1/2}$;
$M^H$=$R^4R^5HSiO_{1/2}$;
$M^E$=$R^6R^7R^ESiO_{1/2}$;
D=$R^8R^9SiO_{2/2}$;
$D^H$=$R^{10}HSiO_{2/2}$;
$D^E$=$R^{11}R^ESiO_{2/2}$;
T=$R^{12}SiO_{3/2}$;
$T^H$=$HSiO_{3/2}$;
$T^E$=$R^ESiO_{3/2}$; and
Q=$SiO_{4/2}$;
where $R^1$, $R^2$, $R^3$, $R^8$, $R^9$ and $R^{12}$ are independently monovalent hydrocarbon radicals having from one to sixty carbon atoms; $R^4$, $R^5$ and $R^{10}$ are independently monovalent hydrocarbon radicals having from one to sixty carbon atoms or hydrogen; $R^6$, $R^7$, $R^{11}$ are independently monovalent hydrocarbon radicals having from one to sixty carbon atoms or $R^E$; each $R^E$ is independently a monovalent hydrocarbon radical containing one or more oxirane moieties having from one to sixty carbon atoms; the stoichiometric subscripts a, b, c, d, e, f, g, h, i, and j are either zero or positive subject to the following limitations: a+b+c>1; b+e+h>1; c+f+i>1; b+e+h>c+f+i.

22. The composition of claim 21 where $R^E$ has the formula:

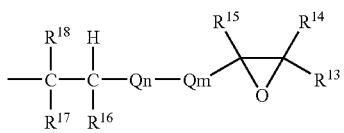

where $R^{13}$, $R^{14}$, $R^{15}$, $R^{16}$, $R^{17}$ and $R^{18}$ are each independently selected from the group of hydrogen and monovalent hydrocarbon radicals having from one to sixty carbon atoms, $Q_m$ is a di- or trivalent hydrocarbon radical having from one to sixty carbon atoms, $Q_n$ is a divalent hydrocarbon radical having from one to sixty carbon atoms with the subscripts m and n independently zero or one subject to the limitation that when Qm is trivalent one of $R^{13}$ or $R^{14}$ is absent.

23. The composition of claim 21 where $R^E$ is obtained by hydrosilylation of a compound selected from the group consisting of 4-vinyl cyclohexene oxide, allyl glycidyl ether, limonene oxide, 1,2-epoxy-5-hexene, 1,2-epoxy-7-octene, norbornadiene monoepoxide and 1,2-epoxy-9-decene.

24. The composition of claim 22 where $R^{13}$, $R^{14}$, $R^{15}$, $R^{16}$, $R^{17}$ and $R^{18}$ are hydrogen and m and n are zero.

25. The composition of claim 23 where $R^E$ is obtained by hydrosilylation of 4-vinyl cyclohexene oxide.

26. The composition of claim 21 where $R^1$, $R^2$, $R^3$, $R^8$, $R^9$ and $R^{12}$ are independently selected from the group consisting of methyl, ethyl, sec-butyl, tert-butyl, octyl, decyl, dodecyl, cetyl, stearyl, ethenyl, propenyl, butynyl, hydroxypropyl, cyanoethyl, butoxy, 2,5,8-trioxadecanyl, carboxymethyl, chloromethyl, C30+ and 3,3,3-fluoropropyl.

27. The composition of claim 22 where $R^1$, $R^2$, $R^3$, $R^8$, $R^9$ and $R^{12}$ are independently selected from the group consisting of methyl, ethyl, sec-butyl, tert-butyl, octyl, decyl, dodecyl, cetyl, stearyl, ethenyl, propenyl, butynyl, hydroxypropyl, butoxy, 2,5,8-trioxadecanyl, carboxymethyl, chloromethyl and 3,3,3-fluoropropyl.

28. The composition of claim 23 where $R^1$, $R^2$, $R^3$, $R^8$, $R^9$ and $R^{12}$ are independently selected from the group consisting of methyl, ethyl, sec-butyl, tert-butyl, octyl, decyl, dodecyl, cetyl, stearyl, ethenyl, propenyl, butynyl, hydroxypropyl, cyanoethyl, butoxy, 2,5,8-trioxadecanyl, carboxymethyl, chloromethyl and 3,3,3-fluoropropyl.

29. The composition of claim 24 where $R^1$, $R^2$, $R^3$, $R^8$, $R^9$ and $R^{12}$ are independently selected from the group consisting of methyl ethyl sec-butyl, tert-butyl, octyl, decyl, dodecyl, cetyl, stearyl, ethenyl, propenyl, butynyl, hydroxypropyl, cyanoethyl, butoxy, 2,5,8-trioxadecanyl, carboxymethyl, chloromethyl and 3,3,3-fluoropropyl.

30. The composition of claim 25 where $R^1$, $R^2$, $R^3$, $R^8$, $R^9$ and $R^{12}$ are independently selected from the group consisting of methyl, ethyl, sec-butyl, tert-butyl, octyl, decyl, dodecyl, cetyl, stearyl, ethenyl, propenyl, butynyl, hydroxypropyl, cyanoethyl, butoxy, 2,5,8-trioxadecanyl, carboxymethyl, chloromethyl and 3,3,3-fluoropropyl.

31. A non-aqueous emulsion where the discontinuous phase comprises a non-aqueous hydroxylic solvent and the continuous phase comprises a composition comprising the reaction product of:

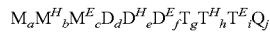

where
M=$R^1R^2R^3SiO_{1/2}$;
$M^H$=$R^4R^5HSiO_{1/2}$;
$M^E$=$R^6R^7R^ESiO_{1/2}$;
D=$R^8R^9SiO_{2/2}$;
$D^H$=$R^{10}HSiO_{2/2}$;
$D^E$=$R^{11}R^ESiO_{2/2}$;
T=$R^{12}SiO_{3/2}$;
$T^H$=$HSiO_{3/2}$;
$T^E$=$R^ESiO_{3/2}$; and
Q=$SiO_{4/2}$;
where $R^1$, $R^2$, $R^3$, $R^8$, $R^9$ and $R^{12}$ are independently monovalent hydrocarbon radicals having from one to sixty carbon atoms; $R^4$, $R^5$ and $R^{10}$ are independently monovalent hydrocarbon radicals having from one to sixty carbon atoms or hydrogen; $R^6$, $R^7$, $R^{11}$ are independently monovalent hydrocarbon radicals having from one to sixty carbon atoms or $R^E$; each $R^E$ is independently a monovalent hydrocarbon radical containing one or more oxirane moieties having from one to sixty carbon atoms; the stoichiometric subscripts a, b, c, d, e, f, g, h, i, and j are either zero or positive subject to the following limitations: a+b+c>1; b+e+h>1; c+f+i>1; b+e+h>c+f+i.

32. The composition of claim 31 where $R^E$ has the formula:

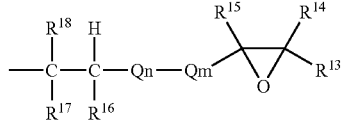

where $R^{13}$, $R^{14}$, $R^{15}$, $R^{16}$, $R^{17}$ and $R^{18}$ are each independently selected from the group of hydrogen and monovalent hydrocarbon radicals having from one to sixty carbon atoms, $Q_n$ is a di- or trivalent hydrocarbon radical having from one to sixty carbon atoms, $Q_m$ is a divalent hydrocarbon radical having from one to sixty carbon atoms with the subscripts m and n independently zero or one subject to the limitation that when Qm is trivalent one of $R^{13}$ or $R^{14}$ is absent.

33. The composition of claim 31 where $R^E$ is obtained by hydrosilylation of a compound selected from the group consisting of 4-vinyl cyclohexene oxide, aHyl glycidyl ether, limonene oxide, 1,2-epoxy-5-hexene, 1,2-epoxy-7-octene, norbornadiene monoepoxide and 1,2-epoxy-9-decene.

34. The composition of claim 32 where $R^{13}$, $R^{14}$, $R^{15}$, $R^{16}$, $R^{17}$ and $R^{18}$ are hydrogen and m and n are zero.

35. The composition of claim 33 where $R^E$ is obtained by hydrosilylation of 4-vinyl cyclohexene oxide.

36. The composition of claim 31 where $R^1$, $R^2$, $R^3$, $R^8$, $R^9$ and $R^{12}$ are independently selected from the group consisting of methyl, ethyl, sec-butyl, tert-butyl, octyl, decyl, dodecyl, cetyl, stearyl, ethenyl, propenyl, butynyl, hydroxypropyl, butoxy, 2,5,8-trioxadecanyl, carboxymethyl, chloromethyl, C30+ and 3,3,3-fluoropropyl.

37. The composition of claim 32 where $R^1$, $R^2$, $R^3$, $R^8$, $R^9$ and $R^{12}$ are independently selected from the group consisting of methyl, ethyl, sec-butyl, tert-butyl, octyl, decyl, dodecyl, cetyl, stearyl, ethenyl, propenyl, butynyl, hydroxypropyl, cyanoethyl, butoxy, 2,5,8-trioxadecanyl, carboxymethyl, chloromethyl and 3,3,3-fluoropropyl.

38. The composition of claim 33 where $R^1$, $R^2$, $R^3$, $R^8$, $R^9$ and $R^{12}$ are independently selected from the group consisting of methyl, ethyl, sec-butyl, tert-butyl, octyl, decyl, dodecyl, cetyl, stearyl, ethenyl, propenyl, butynyl, hydroxypropyl, cyanoethyl, butoxy, 2,5,8-trioxadecanyl, carboxymethyl, chloromethyl and 3,3,3-fluoropropyl.

39. The composition of claim 34 where $R^1$, $R^2$, $R^3$, $R^8$, $R^9$ and $R^{12}$ are independently selected from the group consisting of methyl, ethyl, sec-butyl, tert-butyl, octyl, decyl, dodecyl, cetyl, stearyl, ethenyl, propenyl, butynyl, hydroxypropyl, cyanoethyl, butoxy, 2,5,8-trioxadecanyl, carboxymethyl, chloromethyl and 3,3,3-fluoropropyl.

40. The composition of claim 35 where $R^1$, $R^2$, $R^3$, $R^8$, $R^9$ and $R^{12}$ are independently selected from the group consisting of methyl, ethyl, sec-butyl, tert-butyl, octyl, decyl, dodecyl, cetyl, stearyl, ethenyl, propenyl, butynyl, hydroxypropyl, cyanoethyl, butoxy, 2,5,8-trioxadecanyl, carboxymethyl, chloromethyl and 3,3,3-fluoropropyl.

41. A non-aqueous emulsion where the continuous phase comprises a non-aqueous hydroxylic solvent and the discontinuous phase comprises a composition comprising the reaction product of:

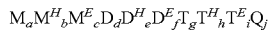

where
$M=R^1R^2R^3SiO_{1/2}$;
$M^H=R^4R^5HSiO_{1/2}$;
$M^E=R^6R^7R^ESiO_{1/2}$;
$D=R^8R^9SiO_{2/2}$;
$D^H=R^{10}HSiO_{2/2}$;
$D^E=R^{11}R^ESiO_{2/2}$;
$T=R^{12}SiO_{3/2}$;
$T^H=HSiO_{3/2}$;
$T^E=R^ESiO_{3/2}$; and
$Q=SiO_{4/2}$; and where $R^1$, $R^2$, $R^3$, $R^8$, $R^9$ and $R^{12}$ are independently monovalent hydrocarbon radicals having from one to sixty carbon atoms; $R^4$, $R^5$ and $R^{10}$ are independently monovalent hydrocarbon radicals having from one to sixty carbon atoms or hydrogen; $R^6$, $R^7$, $R^{11}$ are independently monovalent hydrocarbon radicals having from one to sixty carbon atoms or $R^E$; each $R^E$ is independently a monovalent hydrocarbon radical containing one or more oxirane moieties having from one to sixty carbon atoms; the stoichiometric subscripts a, b, c, d, e, f, g, h, i, and j are either zero or positive subject to the following limitations: a+b+c>1; b+e+h1; c+f+i>1; b+e+h>c+f+i.

42. The composition of claim 41 where $R^E$ has the formula:

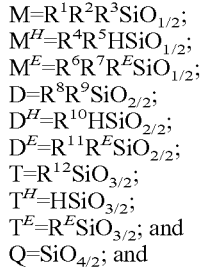

where $R^{13}$, $R^{14}$, $R^{15}$, $R^{16}$, $R^{17}$ and $R^{18}$ are each independently selected from the group of hydrogen and monovalent hydrocarbon radicals having from one to sixty carbon atoms, $Q_m$ is a di- or trivalent hydrocarbon radical having from one to sixty carbon atoms, $Q_n$ is a divalent hydrocarbon radical having from one to sixty carbon atoms with the subscripts m and n independently zero or one subject to the limitation that when Qm is trivalent one of $R^{13}$ or $R^{14}$ is absent.

43. The composition of claim 31 where $R^E$ is obtained by hydrosilylation of a compound selected from the group consisting of 4-vinyl cyclohexene oxide, allyl glycidyl ether, limonene oxide, 1,2-epoxy-5-hexene, 1,2-epoxy-7-octene, norbornadiene monoepoxide and 1,2-epoxy-9-decene.

44. The composition of claim 42 where $R^{13}$, $R^{14}$, $R^{15}$, $R^{16}$, $R^{17}$ and $R^{18}$ are hydrogen and m and n are zero.

45. The composition of claim 43 where $R^E$ is obtained by hydrosilylation of 4-vinyl cyclohexene oxide.

46. The composition of claim 41 where $R^1$, $R^2$, $R^3$, $R^8$, $R^9$ and $R^{12}$ are independently selected from the group consisting of methyl, ethyl, sec-butyl, tert-butyl, octyl, decyl, dodecyl, cetyl, stearyl, ethenyl, propenyl, butynyl, hydroxypropyl, butoxy, 2,5,8-trioxadecanyl, carboxymethyl, chloromethyl, C30+> and 3,3,3-fluoropropyl.

47. The composition of claim 42 where $R^1$, $R^2$, $R^3$, $R^8$, $R^9$ and $R^{12}$ are independently selected from the group consisting of methyl, ethyl, sec-butyl, tert-butyl, octyl, decyl, dodecyl, cetyl, stearyl ethenyl, propenyl, butynyl, hydroxypropyl, cyanoethyl, butoxy, 2,5,8-trioxadecanyl, carboxymethyl, chloromethyl and 3,3,3-fluoropropyl.

48. The composition of claim 43 where $R^1$, $R^2$, $R^3$, $R^8$, $R^9$ and $R^{12}$ are independently selected from the group consisting of methyl, ethyl, sec-butyl, tert-butyl, octyl, decyl, dodecyl, cetyl, stearyl, ethenyl, propenyl, butynyl, hydroxypropyl, cyanoethyl, butoxy, 2,5,8-trioxadecanyl, carboxymethyl, chloromethyl and 3,3,3-fluoropropyl.

49. The composition of claim 44 where $R^1$, $R^2$, $R^3$, $R^8$, $R^9$ and $R^{12}$ are independently selected from the group consisting of methyl ethyl, sec-butyl, tert-butyl, octyl, decyl, dodecyl, cetyl, stearyl, ethenyl, propenyl, butynyl, hydroxypropyl, cyanoethyl, butoxy, 2,5,8-trioxadecanyl, carboxymethyl, chloromethyl and 3,3,3-fluoropropyl.

50. The composition of claim 45 where $R^1$, $R^2$, $R^3$, $R^8$, $R^9$ and $R^{12}$ are independently selected from the group consisting of methyl, ethyl, sec-butyl, tert-butyl, octyl, decyl, dodecyl, cetyl, stearyl, ethenyl, propenyt, butynyl, hydroxypropyl, cyanoethyl, butoxy, 2,5,8-trioxadecanyl, carboxymethyl, chloromethyl and 3,3,3-fluoropropyl.

* * * * *